(12) United States Patent
Wainscott et al.

(10) Patent No.: US 9,327,099 B2
(45) Date of Patent: May 3, 2016

(54) MEDICAL TUBE HARNESS

(71) Applicant: Spectrum Health Innovations, LLC, Grand Rapids, MI (US)

(72) Inventors: Teresa Lynn Wainscott, Ada, MI (US); Andrew John Rodenhouse, Grand Rapids, MI (US); Andrew John Vander Moren, Grand Rapids, MI (US); Asghar Khaghani, Grand Rapids, MI (US); Richard Allen Kanten, Hudsonville, MI (US); Ryan Anthony Bozio, Holland, MI (US)

(73) Assignee: Spectrum Health Innovations, LLC, Grand Rapids, MI (US)

( * ) Notice: Subject to any disclaimer, the term of this patent is extended or adjusted under 35 U.S.C. 154(b) by 197 days.

(21) Appl. No.: 14/294,645

(22) Filed: Jun. 3, 2014

(65) Prior Publication Data
US 2014/0358090 A1    Dec. 4, 2014

Related U.S. Application Data

(60) Provisional application No. 61/830,920, filed on Jun. 4, 2013.

(51) Int. Cl.
| | |
|---|---|
| *A61M 5/32* | (2006.01) |
| *A61M 25/02* | (2006.01) |
| *A61M 5/14* | (2006.01) |

(52) U.S. Cl.
CPC ............. *A61M 25/02* (2013.01); *A61M 5/1418* (2013.01); *A61M 2025/0206* (2013.01)

(58) Field of Classification Search
CPC ..................... A61M 25/02; A61M 2025/0206; A61M 5/1418

USPC ......... 224/262, 259, 250, 257, 645, 660, 264; 604/179, 174, 180; 128/DIG. 26; 248/74.3, 69, 205.2; 182/3

See application file for complete search history.

(56) References Cited

U.S. PATENT DOCUMENTS

| | | | | |
|---|---|---|---|---|
| 3,765,421 A | * | 10/1973 | Poprik .................. | A61M 25/02 128/DIG. 26 |
| 3,878,849 A | * | 4/1975 | Muller ................. | A61M 25/02 128/DIG. 26 |
| 4,083,777 A | | 4/1978 | Hutchisson | |
| 4,096,863 A | * | 6/1978 | Kaplan ................ | A61M 25/02 128/DIG. 26 |
| 4,445,894 A | * | 5/1984 | Kovacs ................ | A61M 25/02 128/DIG. 26 |
| 4,571,245 A | * | 2/1986 | Hubbard .............. | A61M 25/02 128/DIG. 26 |
| 4,591,356 A | * | 5/1986 | Christie ............... | A61M 25/02 128/DIG. 26 |
| 4,617,017 A | * | 10/1986 | Hubbard .............. | A61M 25/02 128/DIG. 26 |
| 4,671,787 A | * | 6/1987 | Widman ............... | A61M 25/02 128/DIG. 15 |

(Continued)

OTHER PUBLICATIONS

Terumo Heart DuraHeart™ LVAD (prior art).

(Continued)

*Primary Examiner* — Justin Larson
*Assistant Examiner* — Lester L Vanterpool
(74) *Attorney, Agent, or Firm* — Warner Norcross & Judd LLP (57) ABSTRACT

A medical tube harness that a subject wears to organize, orient and support medical tubes and reduce the potential for unintentional tugging, kinking, and/or dislodging of the tubes as they extend from a subject's internal cavities, organs, orifices and/or anchor sites on the subject. The harness can improve patient comfort and safety, and can provide multiple locations for strategic tube placement.

17 Claims, 7 Drawing Sheets

(56) References Cited

U.S. PATENT DOCUMENTS

| | | | | |
|---|---|---|---|---|
| 4,707,906 | A | * | 11/1987 | Posey .................. A61G 7/0503 128/DIG. 26 |
| 4,795,429 | A | * | 1/1989 | Feldstein .............. A61J 1/1406 128/DIG. 26 |
| 5,082,111 | A | * | 1/1992 | Corbitt, Jr. ............ A61M 25/02 128/DIG. 15 |
| 5,284,470 | A | | 2/1994 | Beltz |
| 5,352,209 | A | * | 10/1994 | Bird ...................... A61M 25/02 128/DIG. 26 |
| 5,496,282 | A | * | 3/1996 | Militzer ................ A61M 25/02 128/DIG. 26 |
| 5,507,460 | A | * | 4/1996 | Schneider ........... A61M 5/1418 24/601.2 |
| 5,577,653 | A | | 11/1996 | Bieker |
| 5,624,403 | A | * | 4/1997 | Jaquith ................ A61M 25/02 128/DIG. 26 |
| 5,672,159 | A | * | 9/1997 | Warrick ........... A61M 16/0683 128/DIG. 26 |
| 5,709,665 | A | * | 1/1998 | Vergano ............. A61M 5/1418 128/DIG. 26 |
| 5,728,070 | A | | 3/1998 | Walker et al. |
| 5,741,306 | A | | 4/1998 | Glegyak et al. |
| 5,776,105 | A | * | 7/1998 | Corn ................... A61M 5/1483 604/174 |
| 5,897,519 | A | * | 4/1999 | Shesol ................. A61M 25/02 602/75 |
| 6,270,485 | B1 | * | 8/2001 | Ekey .................... A61F 5/4408 224/663 |
| 6,289,896 | B1 | | 9/2001 | Hart |
| 6,645,185 | B2 | * | 11/2003 | Bird ...................... A61M 25/02 604/179 |
| 6,811,749 | B2 | | 11/2004 | Lindsay |
| 7,588,216 | B1 | * | 9/2009 | Hoyl ........................ H02G 3/30 174/50 |
| D621,502 | S | | 8/2010 | Downs |
| 7,927,311 | B1 | | 4/2011 | Bachelder |
| 8,177,736 | B2 | * | 5/2012 | Kopperschmidt .. A61M 1/3653 24/335 |
| 8,226,621 | B2 | * | 7/2012 | Timmons ............... A61F 5/4408 604/327 |
| 2005/0059935 | A1 | * | 3/2005 | Yamazaki ........... A61M 1/3661 604/179 |
| 2006/0054387 | A1 | * | 3/2006 | Fortin ................ A62B 35/0025 182/3 |
| 2006/0113432 | A1 | | 6/2006 | Driskell |
| 2007/0272484 | A1 | * | 11/2007 | Helms ................ A62B 35/0018 182/3 |
| 2008/0210828 | A1 | * | 9/2008 | Kogure ................ H02G 11/006 248/65 |
| 2009/0070912 | A1 | * | 3/2009 | Wolfe ................ A41D 13/0007 2/69 |
| 2009/0095858 | A1 | * | 4/2009 | Katou ................ B60R 16/0215 248/205.1 |
| 2010/0072241 | A1 | | 3/2010 | Brown et al. |
| 2010/0114001 | A1 | | 5/2010 | O'Mahony |
| 2010/0122995 | A1 | | 5/2010 | Thomas et al. |
| 2010/0325772 | A1 | | 12/2010 | Fladl et al. |
| 2011/0023208 | A1 | | 2/2011 | Liao |
| 2011/0160516 | A1 | | 6/2011 | Dague et al. |

OTHER PUBLICATIONS

Thoratec HeartMate II® Left Ventricular Assist Device (prior art).
Belts, vests, harnesses, 8 pages (prior art).
Tubing clips, 5 pages (prior art).

* cited by examiner

MEDICAL TUBE HARNESS

BACKGROUND OF THE INVENTION

The present invention relates to a harness for organizing and supporting components on a subject, and more particularly to a tube harness that supports and organizes medical tubes associated with a subject.

There are a variety of surgical procedures and other treatments that result in or require the installation of medical tubes to assist in bodily functions. For example, medical tubes can be used for various functions, such as blood circulation, cardiovascular support, intravenous administration of drugs and/or the drainage of fluids from the body of the subject. Typically, medical tubes are anchored to an exit location on a subject's skin so that the tube does not dislodge from the skin or an internal organ.

An issue with medical tubes, however, is that they can inadvertently be tugged or pulled, which in turn stresses the anchor site of the tubes and the tubes' connections to internal organs. In some cases, tugging or movement of the tubes at the anchor site can result in infection at the site, or great bodily harm to the subject if a tube is associated with sustained cardiac function. Consequently, there exists a risk of tug trauma at the anchor site of the medical tubes, as well as to the organ to which the tubes are connected.

There are some vest-like constructions directed to addressing tug trauma. One such construction is shown in U.S. Published Application 2011/0023208 to Liao, which is incorporated by reference herein. Vests like those of Liao, however, can suffer some shortcomings in that the tubes are constrained to a general linear, vertical direction exiting the subject. Further, the vest normally secures many of the tubes in a fixed location directly in front of the subject. While this construction is helpful, there remains room for improvement in the field of harnesses that secure and organize medical tubes to improve mobility and safety.

SUMMARY OF THE INVENTION

A tube harness is provided to organize, support and/or redirect medical tubes that are anchored or otherwise installed relative to a subject.

In one embodiment, the harness can include one or more of a belt, suspenders and garters, to which one or more tube guides are rotationally and/or modularly attached.

In another embodiment, a tube guide of the harness can include a concave and/or U-shaped groove or channel for capturing and redirecting a tube from a first direction to a second direction. A rotational element can enable the tube guide, with a tube loaded thereon, to rotate about an axis of rotation so that the tube does not tug relative to the subject and/or an anchor site of the subject.

In still another embodiment, the tube guide can include one or more tube locks that position and secure the tube in a fixed position relative to the tube guide when the tube is positioned in the concave groove.

In yet another embodiment, the groove or channel of the tube guide can include inner curved contours that gradually redirect the tubes from a first axis to a second different axis which is at an angle relative to the first axis. This gradual redirection can prevent kinking of the tubes, which can interrupt flow of fluids within the tube.

In even another embodiment, the tube guides can include a frictional component that increases the friction between the tube guide, for example, the concave groove and the tube, so that the tube does not inadvertently slide relative to the guide.

Optionally, the friction component can be at least one of a ridge, bump, projection or other physical structure extending within the concave groove. The component can engage and effectively grip the tube, preventing it from slipping within the groove. Alternatively, the friction component can be a special coating or texture applied to the inner surface of the groove.

In a further embodiment, the harness can be in the form of a kit. The kit can include multiple tube guides having respective concave grooves with entrances and exits offset at different angles so that a tube disposed in the groove is reoriented from one axis to another, different axis. As one example, a first tube guide can reorient a tube so that it is redirected from a first axis to a second axis that is 45° offset from the first axis. As another example, a different tube guide can reorient a tube so that it is redirected from a first axis to a third axis that is 90° offset from the fixed axis. Other tube guides can be offset at other different angles depending on the desired reorientation of the tube and its ultimate direction to and from the patient and/or an associated device connected to the tubes.

In still a further embodiment, the harness can include mounting elements associated with the belt, shoulder straps and/or garters. The mounting elements can be configured so that some of them have locking elements to temporarily secure the tube guide rotationally connected to the mounting elements and thus the respective belt, shoulder strap and/or garters. Optionally, the garters can include mounting elements that do not have a locking element or otherwise include an easy-release locking element. In this manner, when a subject wearing the harness, and having medical tubes protruding from or otherwise associated with their body, transitions to a particular position, such as a seated position, the tube guides disassociate or otherwise release from the mounting elements on the garters so that those tubes do not otherwise tug at the anchor sites of the medical tubes, thereby causing tug trauma.

The current embodiments provide a tube harness with multiple benefits. For example, the harness can organize the medical tubes, thereby simplifying treatment of a subject utilizing the tubes. The harness can support the medical tubes in a predetermined, fixed orientation to prevent or impair the tubes from inadvertently being moved or pulled out from an anchor site of the subject. The harness can offer variability in the placement of the tubes to accommodate a variety of different physical characteristics of subjects as well as anchor sites of particular medical tubes.

These and other objects, advantages, and features of the invention will be more fully understood and appreciated by reference to the description of the current embodiments and the drawings.

Before the embodiments are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from

DETAILED DESCRIPTION OF THE CURRENT EMBODIMENTS

A medical tube harness and related kit for use with medical tubes is illustrated in FIGS. 1-8 and generally designated 10. The harness can include one or more components, for example, a belt 20, one or more shoulder straps 30 and one or more leg garters 40. Although shown with these components, the harness and/or a kit associated therewith can include a belt that can be used in any combination with the suspenders and/or garters, and/or these components can be used separately and individually. For example, one harness can include a belt 20 and suspenders 30, and another can include the belt 20 and the garters 40. Optionally, the belt 20 can be used alone or in every combination as an optional mainstay of holding the medical tubes in a predetermined configuration, organizing them and supporting them appropriately.

Figure 1:
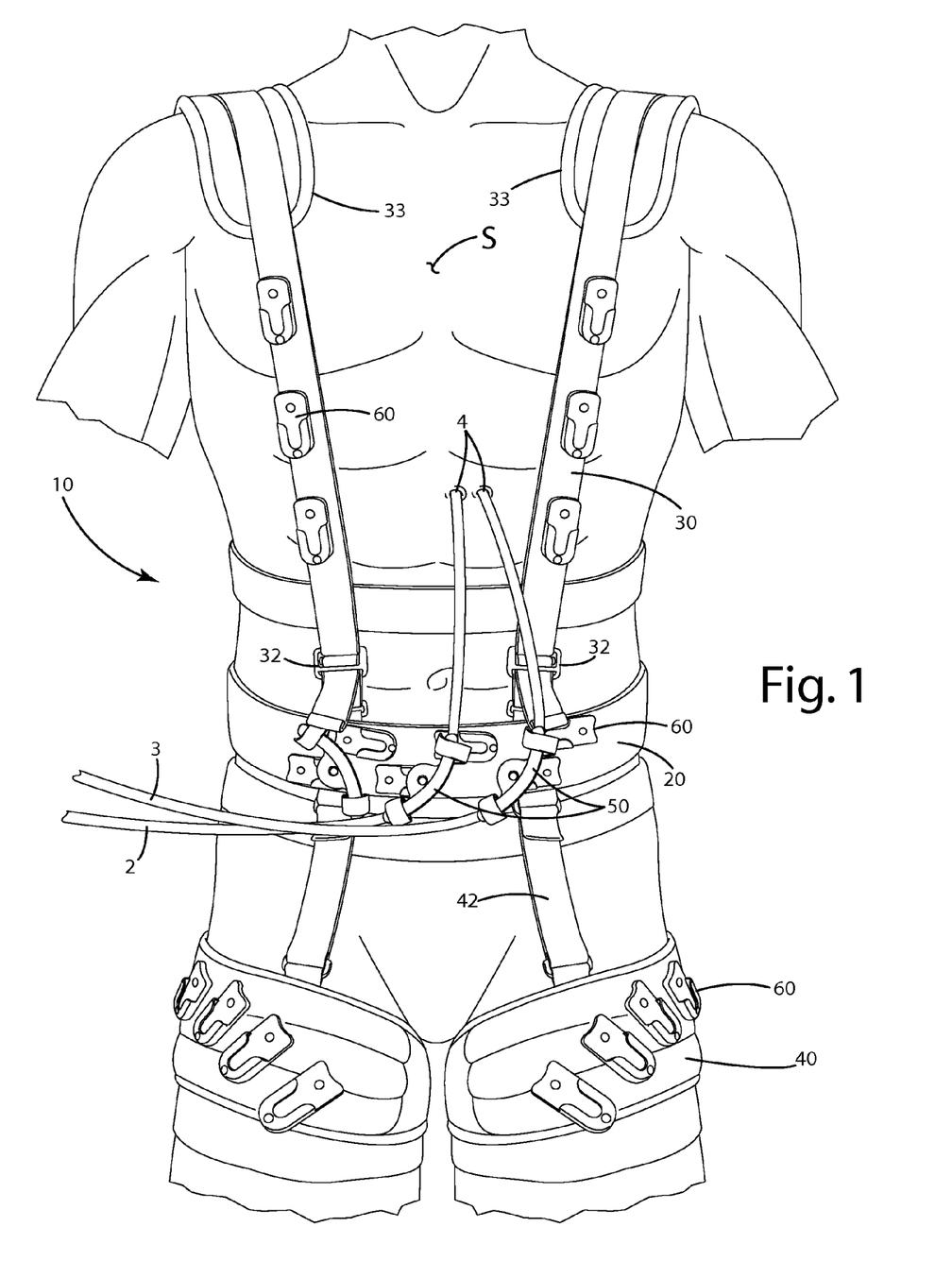
FIG. 1 is a front perspective view of a tube harness of a current embodiment on a subject with tubes projecting from the subject's torso and held by the tube harness.

As illustrated in FIG. 1, the harness can be used in connection with supporting medical tubes associated with a Paracorporeal Ventricular Assist Device (PVAD). A PVAD typically includes multiple tubes 2, 3 that are implanted at anchor sites 4 of the chest, abdomen and/or torso and extend through the subject's skin. The tubes can extend to an external, standalone, generally non-portable pump that is mounted on a cart. Of course, the current embodiment can be used in connection with smaller portable PVADs, for example those offered by Thoratec Corporation of Pleasanton, Calif.

Further, although described generally in connection with a PVAD herein, the harness can be used with tubes in any type of medical treatment that utilizes medical tubing where it is desired to reduce the risk of tug trauma associated with the tubes and/or unintentional dislocation of the tubes, or otherwise organize and/or support the medical tubing. For example, the harness can be used with certain medical tubing associated with hemodialysis, blood circulation, blood withdrawal, chemotherapy, transplants, intravenous feeding and/or drug administration, respiration and/or bodily fluid drainage. Additionally, as used herein, the term tube and/or medical tube can be any type of tubing, wiring, catheter, drain, or any other element or structure which is inserted into a subject's body and is affixed thereto at an anchor site or other access point in or on the skin.

With reference to FIG. 1, the medical tubes 2 and 3 can be associated with a PVAD or some other device associated with medical tubes. The tubes 2 and 3 can transport and/or be filled with blood, and therefore can have weight or mass. Sometimes, the tubes may extend 3 to 6 feet outside the patient to a pump, whether a standalone pump, a cart-mounted pump or a portable pump. The tubes, if draped over the side of a bed, can tug in a direction away from the subject S due to the weight or mass of fluids (such as blood) conveyed therethrough. This can cause tug trauma and/or can cause displacement of the tubes at the anchor sites 4. This can potentially lead to infection or other complications with regard to the tubes and their function relative to the subject S.

In some cases, where it is desired for the patient to be mobile for whatever reason, the tubes something can interfere with the subject's movement. Some research has been performed illustrating better outcomes and shorter hospital stays where subjects are mobilized by being seated, standing or experiencing other movement. However, in simple motions, for example when the subject moves from sitting down to standing up, or laying down to standing up, the tubes can interfere with the subject's leg and/or arm movement. This can be further complicated by the tubes draping over an article of furniture in which the subject is located. If the tubes snag on the furniture, this can cause tug trauma and/or have a life-threatening effect by dislodging the tubes from the subject and/or their internal organs.

Returning to FIGS. 1-3, the belt, shoulder straps and garters can provide several functions. For example, the shoulder strap, when included, can maintain the belt suspended in a desired location, keeping the belt from moving down the waist of the patient, which can pull the medical tubes 2,3 away from the anchor sites 4. The garters 40, when included, can keep the belt 20 from riding up the patient's waist or torso, which again can cause problems by virtue of the belt inadvertently advancing the tubes 2,3 toward and/or into the subject or otherwise dislodging the tubes from the scar tissue around the anchor site 4.

In general, the belt 20 can be of a sufficient length to circumferentiate a particular subject's waist and/or torso. It can include fasteners and/or straps that allow the belt to be fastened around the subject's waist and/or torso. The belt can also be of variable length, to fit subjects of varying girth. The fasteners can include hook and loop fastening systems, such as those sold under the name Velcro®. Alternatively, the fasteners can be in the form of buckles, straps, buttons, eyelets or any other structure capable of holding the belt around the waist and/or torso of the subject.

The shoulder straps 30, when included, can be secured to the belt 20 with adjuster straps 32. The shoulder straps also can be referred to herein as suspenders. The adjuster straps 32 can include fasteners to allow the shoulder straps to be easily removed from the belt. Alternatively, the shoulder straps 30 can be permanently stitched and secured to the belt. The shoulder straps can include padding 33 that is configured to increase the surface area and provide padding where the shoulder straps engage the subject's shoulders. This can reduce fatigue and can improve the comfort of the shoulder straps 30.

The leg garters 40 can include garter straps 42. The garters 40 can be secured or otherwise joined with straps 42 to the belt 20. The straps 42 can be configured to be adjustable in length and/or removable like the straps 32 above. The leg garters 40 can include one or more fasteners that enable them to be wrapped around a user's leg and fastened end to end or end over end to secure the garter to the subject's leg. Optionally, the garters can be of a sufficient length and the fasteners can be oriented to accommodate a variety of different leg sizes. The same is true for the belt and shoulder straps.

Generally, the belt 20, shoulder straps 30 and garters 40 can be constructed from a lightweight, breathable material that is able to be washed multiple times after being exposed to bodily fluids. The belt, shoulder straps and garters can be constructed from a variety of fabrics, either woven or non-woven, or other materials depending on the application. Although shown as being black, the harness and its components can be white or some other lighter color to enable users to better identify bodily fluids being disposed on the harness.

Figure 2:
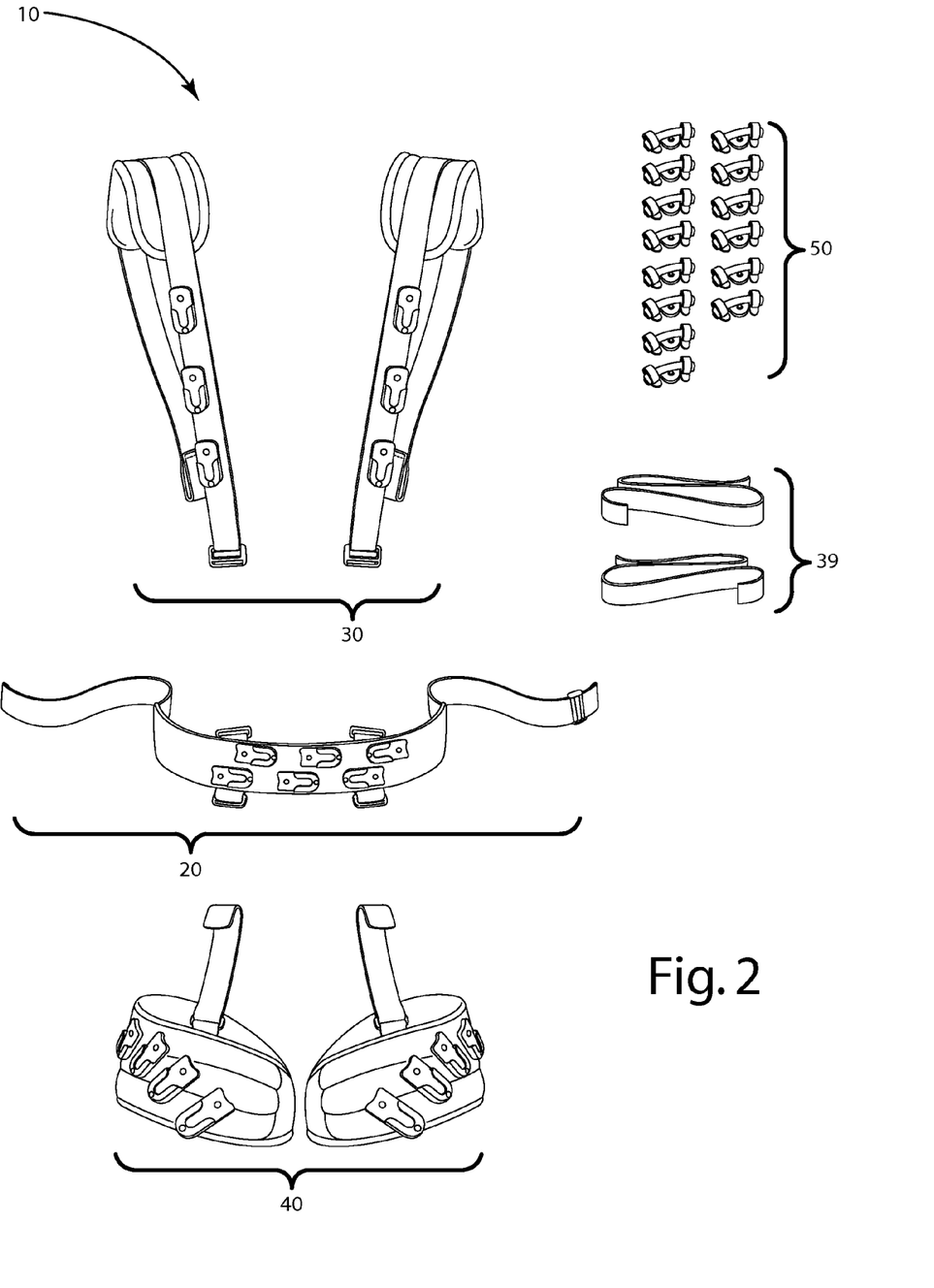
FIG. 2 is a perspective view of various components of the tube harness laid out in a kit form.

Referring to FIG. 2, the harness can come in a kit form with the different components, for example, the belt 20, shoulder straps 30 and garters 40. The kit also can come with a variety of different tube guides 50 and additional support straps 39. These items can be mixed and matched depending on the particular type of medical tube to be joined and otherwise secured in a fixed location on a subject's body, and/or the desired level of tube organization on the subject's body. Further, selected ones of the tube guides 50 can be use depending on the size of the tube, its flexibility and the desired orientation and redirection of the medical tubes relative to the different components.

Figure 3:
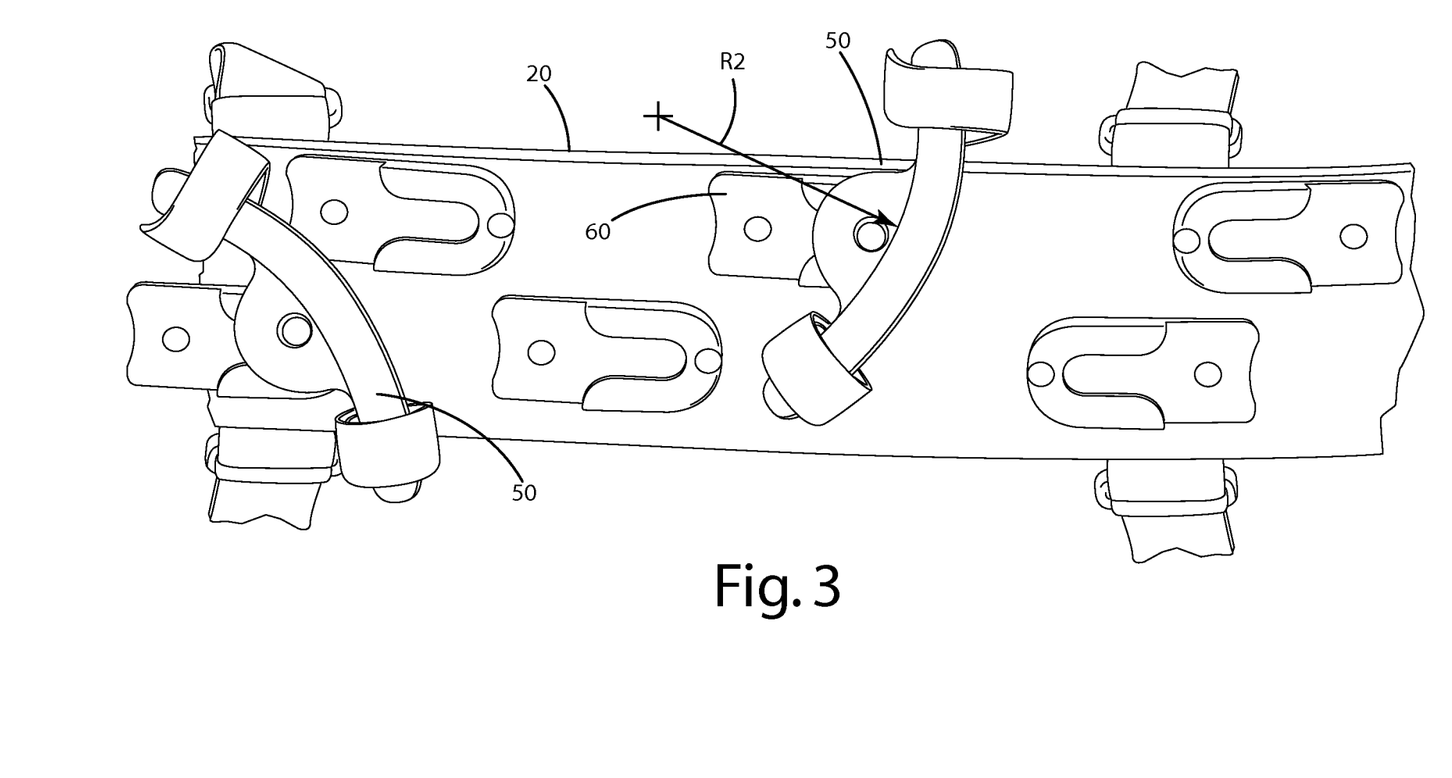
FIG. 3 is a perspective view of a belt of the tube harness including mounting elements and tube guides.
Figure 4:
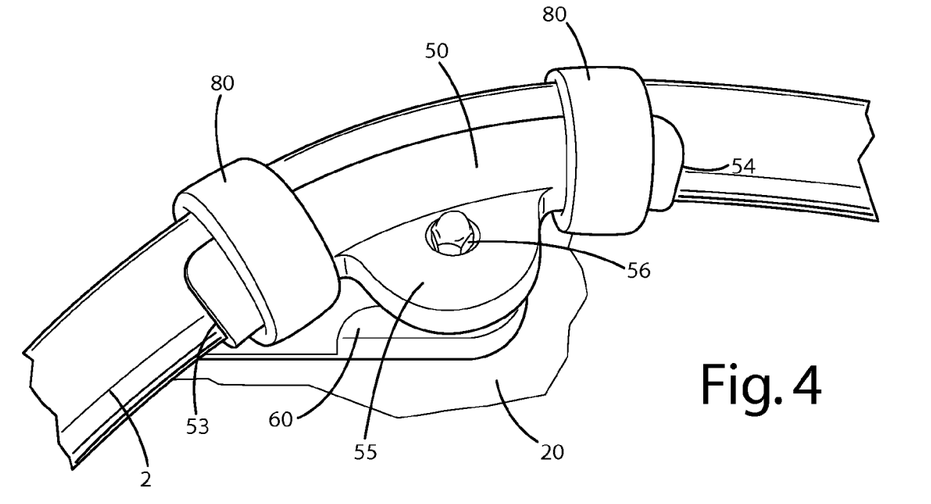
FIG. 4 is a close up view of a tube guide with a tube mounted therein.

As shown in FIG. 3, the tube guides 50 are shown joined with mounting elements 60 further joined to the belt 20. The belt 20 can include multiple mounting elements joined in multiple locations across an outer surface of the belt 20. Generally, when the harness is used, only selected ones of the mounting elements 60 are occupied or otherwise joined with particular tube guides 50. If desired, the tube guides 50 can be selectively placed by a user in locations (and associated with respective mounting elements) that are helpful to organize the medical tubes in a desired orientation. Many of the mounting elements 60 on the belt 20 or on the shoulder straps and/or garters can be empty in use, that is, without tube guides being associated therewith.

Figure 5:
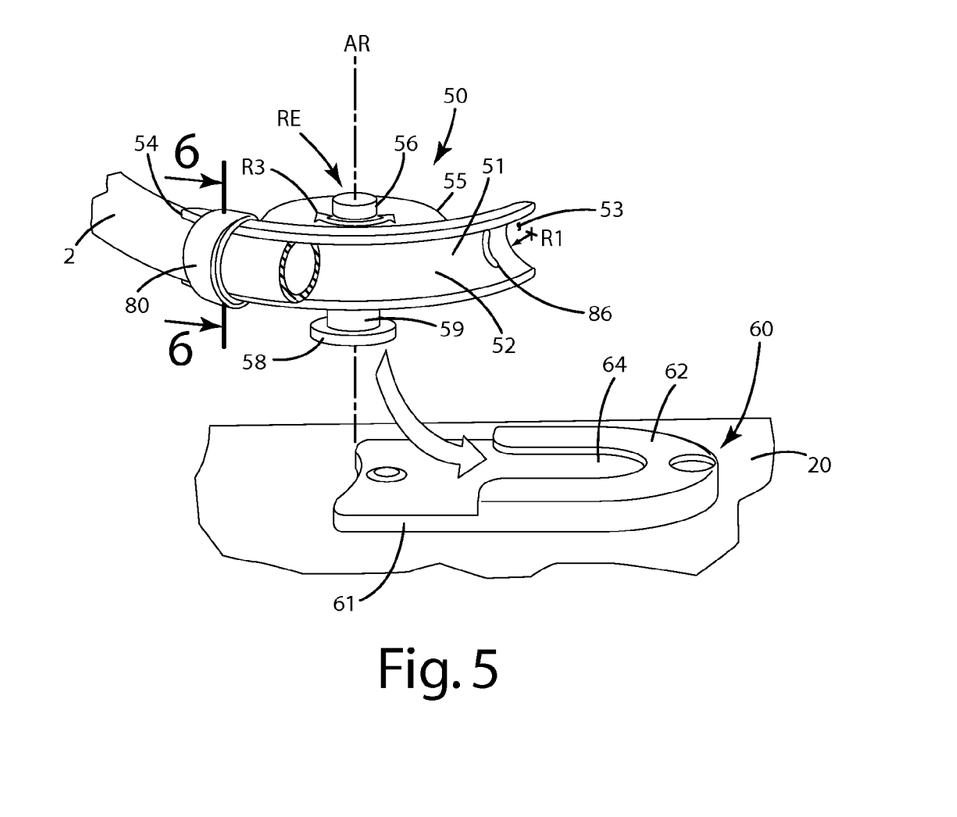
FIG. 5 is a perspective view of a tube guide with a tube mounted therein being joined with a mounting element.
Figure 7:
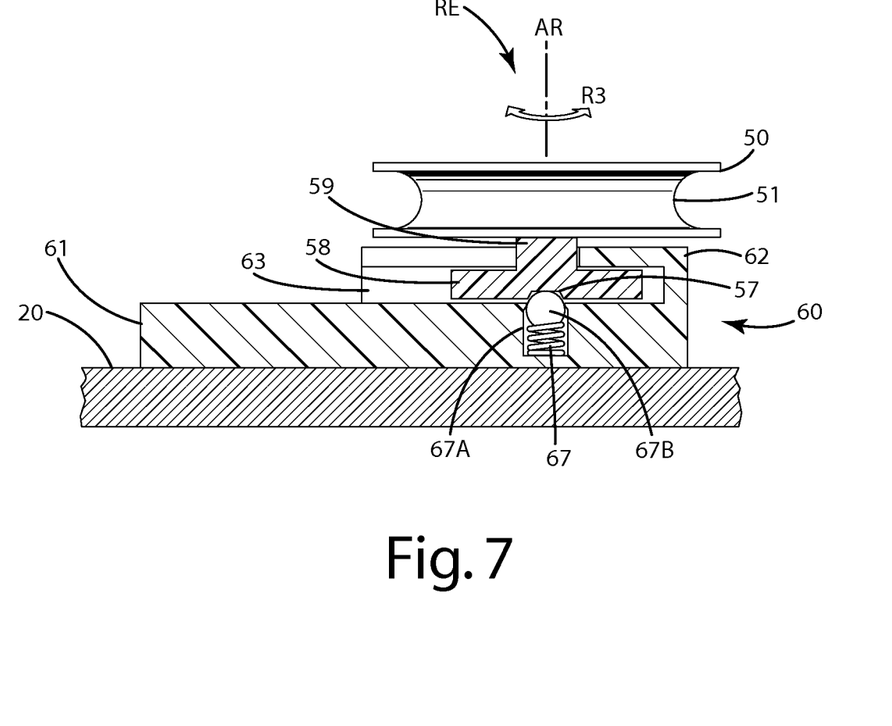
FIG. 7 is a section view of a mounting element with a tube guide installed relative to the mounting element.

An exemplary mounting element is shown in FIG. 5. The mounting element 60 can be attached to the underlying belt 20 or other structure, such as the shoulder straps and/or garters, via fasteners, glue or any other element. The mounting element 60 can include a base 61 and an upper plate 62. The base can be fastened to the belt's surface. With further reference to FIG. 7, the mounting element 60 also can define a capture cavity 63. The capture cavity 63 can be located between the upper plate 62 and the base 61 and further optionally confined by respective walls on opposite sides. The mounting element 60 also can define a slot 64 that opens to the capture cavity. This slot 64 can be configured to accommodate a post or fastener 59 of the tube guide 50 so that the post or fastener 59 can slide into and out from the slot.

Optionally, the mounting element can include a locking element 67. As shown in FIG. 7, the locking element can engage the post 59 or otherwise engage an enlarged head 58 associated with the post and/or tube guide 50. This optional locking element 67 can engage the enlarged head 58 and/or post 59 to temporarily secure the guide 50 to the mounting element 60. Optionally, the locking element can include a spring 67A that presses or urges a plunger 67B upward. The plunger can engage a recess 57, depression or other feature in the enlarged head 58. Upon this engagement, the plunger 67B can temporarily hold the tube guide 50 joined with the mounting element 60. The spring 67, and generally the locking element, can be configured so that with minimal force, for example, about 0.5 to 10 pounds, further optionally, about 1 to 2 pounds, a user can disengage the locking element 67B from the enlarged head 58, and generally release the tube guide 50 from the mounting element 60. In some cases, as described below, the mounting element 60 can be void of any type of locking element 67. Optionally, the locking element as shown can be replaced with any structure that enables the tube guide 50 to secure to and/or release from the mounting element 60.

Figure 6:
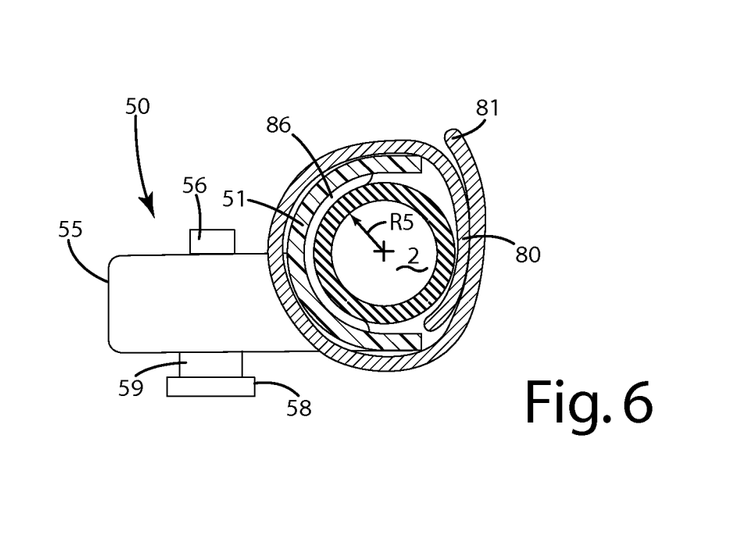
FIG. 6 is a section view taken along lines 6-6 of FIG. 5.

As illustrated in FIGS. 5-7, the tube guide 50 can define a concave groove 51. This concave groove 51 can be of a U-shape, V-shape, channel shape or other geometric shape depending on the particular configuration. The concave groove can include a first radius R1 as shown in FIG. 5. A first radius can match or can be larger than a cross sectional radius R5 (FIG. 6) of a tube 2 that is mounted within or otherwise joined with a tube guide 50.

The concave groove 51 can include an inner contour 52 that generally spans from the entrance 53 to the exit 54 of the tube guide 50. The distance between the entrance and the exit can vary, but can be optionally from about 2" to about 6", about 2½" to about 4", and further optionally about 3", depending on the particular application and/or the size of medical tube used.

Figure 10:
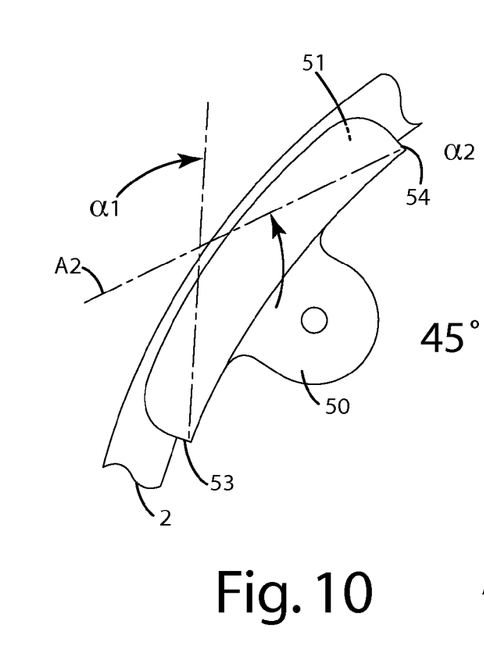
FIG. 10 is a top view of a tube guide having a first orientation angle.

The entrance 53 and exit 54 can be offset at an angle relative to one another so that the tube is reoriented within the concave groove from a first direction to a second direction by the tube guide 50. This is illustrated with a further reference to FIG. 10. There, the concave groove or channel 51 can define a first axis A1 located at the entrance 53 of the groove. This axis A1 can generally correspond to a tangential line defined by the bottommost portion of the groove 51 in that location. The exit 54 of the groove can define a second axis A2, which can generally correspond to a line drawn tangential to the bottom of the groove at the exit 54. The first axis A1 and the second axis A2 can be offset from one another by an angle $\alpha 1$. This angle $\alpha 1$ as shown can be 45°. Of course if desired, that angle can be any other angle depending on the particular size and type of tube 2 used in connection with the tube guide 50, or other considerations such as the weight of the tube 2, the stature of the subject, and/or the particular orientation of the tube 2 relative to an anchor site and/or a tube guide associated with the tube.

As shown in FIG. 5, the inner contour 52 of the groove 51 is selected to prevent and/or impair kinking of the tube 2 to which in some cases could be catastrophic for the subject. Further, the inner contour 52 and radius R1 of the groove can be selected to generally increase the friction between the guide and the tube so that the tube does not inadvertently slide within the guide, to ensure a consistent and secured distance between the guide and the anchor site 4 and/or the pump or other device associated with the tube.

Figure 11:
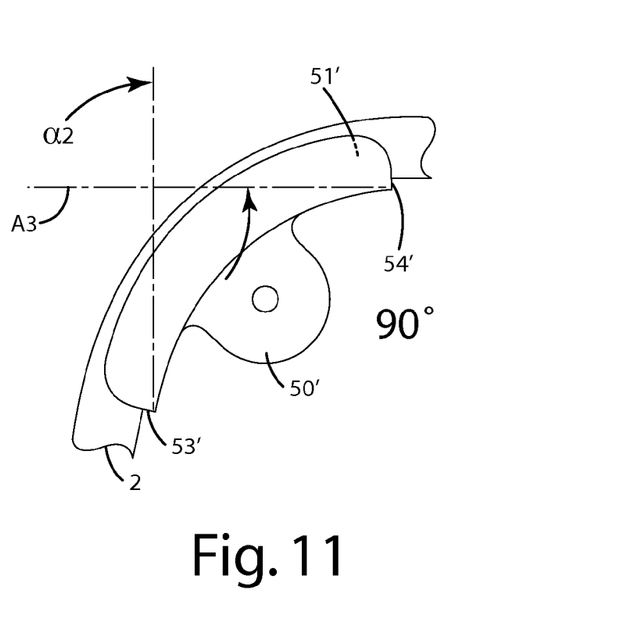
FIG. 11 is a top view of a second tube guide having a second orientation angle.

Optionally, tube guides 50 can come in a variety of different configurations to provide specific reorientations or redirections of the tube 2 guided within the groove thereof. For example, as shown in FIG. 11, the tube guide 50' can include a concave groove 51' including a second entrance 53' and a second exit 54'. The entrance and exit can be offset at an angle $\alpha 2$ relative to one another so that the tube within the groove 51' is reoriented from the first axis A1 to a third, different axis A3 by the tube guide 50'. This second angle $\alpha 2$ can be, for example, 90°. Thus, the tube guide 50' can reorient the tube from a first direction to a second different direction that can be perpendicular to the first direction when transitioning through the tube guide 50', and in particular the concave groove 51'.

Figure 12:
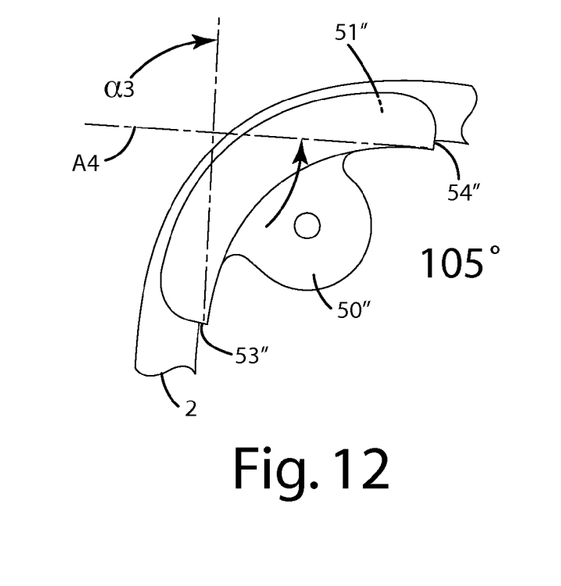
FIG. 12 is a top view of a third tube guide having a third orientation angle.

As another example shown in FIG. 12, the tube guide 50" can have a second concave groove 51" including a third entrance 53" and a third exit 54" offset at an angle α3. This angle α3 can be different from the angles α1 and α2 of the other tube guides 50, 50' shown in FIGS. 10 and 11. Optionally, this other angle α3 can be 105° or some other angle, depending on a particular application. With this tube guide, it can reorient a tube within the groove 51' from a first axis α1 to a fourth axis α4 by the tube guide 50" when the tube is placed in the concave groove 51".

Optionally, the harness 10 can be sold as a kit, as shown in FIG. 2. The kit can include multiple different tube guides configured to include entrances and exits offset at a variety of different angles relative to one another and configured to reorient a tube disposed within the tube guide groove through a variety of different angles and to a variety of different axes. As an example, a kit can come with a variety of different tube guides with different offset angles α1, α2 and α3 generally being 45°, 60°, 75°, 90°, 105° or various other angles depending on the particular application and desired tube organization. The tube guides with varying angles can be mixed and matched, and used with the support components as desired to provide tube organization on the subject.

Returning to FIGS. 5 and 6, the tube guide 50 can include a rotational element that enables the tube guide to rotate relative to the mounting element and/or the belt, shoulder strap and/or garter. In one construction, the rotational element RE can include a flange 55 extending from the concave groove 51. Generally, the flange 55 can extend from a lower or bottom portion of the groove, opposite the inner contour. The flange 55 can define or be joined with the post and/or fastener 59. The flange 55 can define an opening 56 through which the post and or fastener 59 extends. The post and/or fastener 59 joined with the flange can be rotationally or pivotally joined with the flange and/or the mounting element which allows the tube guide 50 to rotate in directions R3 about an axis of rotation AR with the tube 2. The opening 56 can be defined and optionally can be perpendicular to the flange.

As shown as FIGS. 5 and 6, the tube guide 50 can rotate in direction R3 about the axis of rotation. This rotation can occur with the post rotating relative to the flange 55 and/or the post rotating relative to the slot 64 or mounting element 60 in general. As shown in FIG. 7, the locking element 67 does not interfere with the rotation as it is located on the axis of rotation. Of course, if desired, the enlarged head 58 can be rotationally constrained relative to the mounting element 60. This can be accomplished via a fastener or projection that selectively engages the head, preventing it from rotating.

Optionally, the rotation of the tube guide about the axis of rotation AR enables the tube to "float" with regard to the mounting element and more particularly relative to the belt, shoulder strap and/or garter. This can enable the tube guide 50 to reduce any tube disruption forces by simply swiveling or rotating when a subject moves, and thereby reduce tug trauma at the anchor site 4.

The tube guide 50 also can include one or more tube locks 80. These tube locks can control the position of the tube 2 and its length between the tube guide 50 and the anchor site 4 or generally the subject and/or the pump or other device associated with the tube. One optional tube lock is shown in the form of a Velcro® strap that extends around a portion of the tube 2, around the tube guide/groove 51 and overlaps the tube 2. An end 81 of the tube lock 80 can secure to itself or another portion of the strap and thereby clampingly engage or otherwise secure the tube 2 so that it does not move relative to the groove 51 and/or tube guide in general. If desired, the tube lock 80 can be replaced with a piece of tape, a clamp, a latch or other structure that folds or moves over the groove 51 to clampingly or otherwise frictionally engage the tube 2 so that it does not move relative to the groove 51 and the tube guide 50. Respective tube locks 80 can be placed at the entrance 53 and exit 54 of the tube guide 50. More or fewer tube locks can be included on the tube guide as desired.

Optionally, the tube guide 50 can include one or more friction components 86. As shown in FIGS. 5 and 6, the friction component 86 is in the form of a projection that is transverse to the length of the groove 51 and/or the tube 2. This projection can be a ridge of a triangular, square, rounded or other cross sectional shape and can project upwardly from the inner contour 52 of the groove 51. The friction component or projection can project upwardly from the inner contour by about 0.1 mm to about 3 mm, or more or less depending on the particular application. This projection 86 can bite into or otherwise grip the exterior of the tube and assist in holding it in place via friction or other mechanical forces. If desired, the illustrated friction component in the form of a ridge or projection can be replaced with multiple bumps or nodes, or a frictional coating that increases the friction between the tube 2 and the tube guide 50. Alternatively, the tube guide can include a friction component that is made out of a more grippy material, such as thermoplastic polyurethane, or can include a physical feature such as snaked or zigzag tube groove to increase or enhance the friction between the guide and the tube.

The tube guide 50 and/or mounting elements 60 can be constructed from polymers, composites, metals or any other material depending on the particular application. Generally, the tube 2 can be constructed from a slippery polymeric material and becomes even more slippery when warm blood flows through it. Accordingly, the tube lock and/or friction component as described above can impair the sliding of the tube relative to the tube guide 50.

Figure 9:
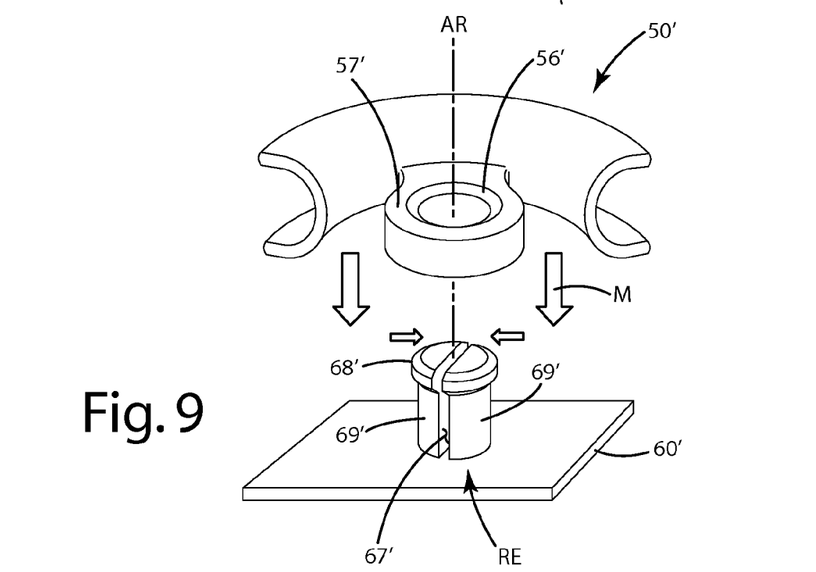
FIG. 9 is a perspective view of a tube guide being joined with a mounting element of a first alternative embodiment.

An alternative embodiment of the mounting element is illustrated in FIG. 9 and generally designated 60'. There, the mounting element 60' includes resilient fingers 69'. These resilient fingers are separated by a groove 67' and terminate at enlarged upper ends or a head 68'. The tube guide 50' can define an opening 56'. The tube guide 50' can be joined to the mounting element 60' by moving the tube guide downward in the direction of the arrows M. When this occurs, the resilient fingers 69 move inward and through the openings 56' until they snap back outward, at which point the enlarged ends or heads 68' engage the perimeter 57' around the opening to secure the tube guide 50' to the mounting element 60'. Even though secured, the tube guide 50' can rotate about the axis AR relative to the mounting element 60'.

Figure 8:
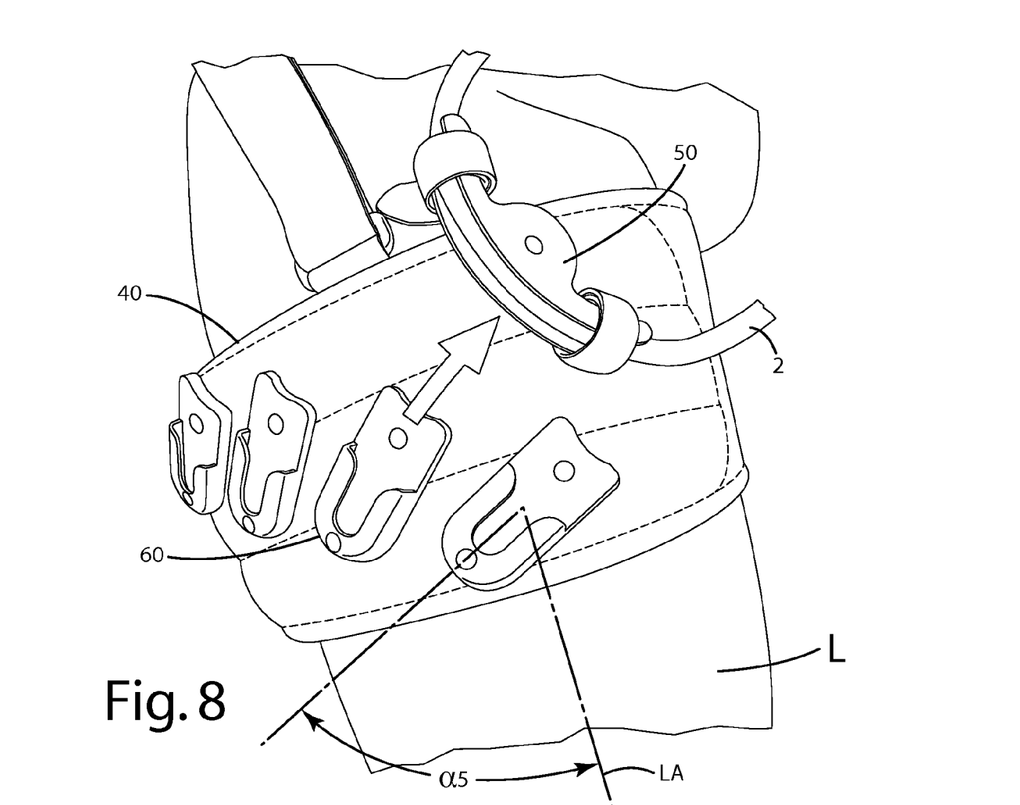
FIG. 8 is a perspective view illustrating a release of a tube guide relative to a mounting element on a garter of the harness.

Optionally, the mounting elements 60 on the garter 40 can be specifically configured. With reference to FIG. 8, those mounting elements 60 can be void of any type of locking element, or generally can require a very low release force (0.01-0.5 pounds) to unlock the locking element and separate the tube guide 50 from the element 60. Accordingly, when a subject sits down or transitions to a sitting position, the tube guide 50 can release from the mounting element 60 in the direction of the arrow shown in FIG. 8. This assures that the tube 2 is not pulled excessively tight, which may cause problems at the anchor site including tug trauma. The mounting elements 60 can be specially mounted at a particular angle α5 relative to the longitudinal axis LA of the subject's leg L so that disengagement of the tube guide 50 from the mounting element 60 is further assured. This angle α5 can range any-where from 30° to 60°, and optionally about 45°, depending on the particular application and the desired release force to separate the components.

The tube harness and embodiments herein generally: (a) offer a system to organize medical tubes; (b) hold and organizes the tubes in a predetermined, fixed orientation to prevent the tubes from being inadvertently moved relative to or pulled out from a subject; (c) fixedly and rigidly attaches the tubes to the harness so that they cannot be inadvertently moved from a location that keeps them firmly or safely implanted at anchor sites; (d) offers variability in the placement of the medical tubes to accommodate a variety of different subjects and implant location of the tubes; and/or (e) provides a variety of mounting locations for the tube guides.

All patents, patent applications, and literature references cited in this specification are hereby incorporated herein by reference in their entirety. In case of conflict, the present description, including definitions, will control.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The embodiments of the invention in which an exclusive property or privilege is claimed are defined as follows:

1. A medical tube harness adapted for use on a subject, the harness comprising:
    at least one of a belt shaped and sized to engage at least one of a subject's waist and torso, a shoulder strap shaped and sized to engage the subject's shoulder, and a leg garter shaped and sized to engage the subject's leg;
    at least one tube guide rotationally attached to at least one of the belt, the shoulder strap and the leg garter,
    wherein the tube guide is modularly moveable to a plurality of different attachment locations on the at least one of the belt, the shoulder strap and the leg garter, to accommodate a plurality of different orientations of a medical tube associated with and extending from the subject;
    wherein the tube guide defines a concave groove capturing and redirecting the tube from a first direction to a second, different direction;
    wherein the tube guide includes a tube lock that immovably secures the tube to the tube guide; and
    wherein the tube guide includes a rotational element that enables the tube guide, with a tube loaded thereon, to rotate about an axis of rotation.

2. The medical tube harness of claim 1,
    wherein the tube lock includes a strap that wraps at least partially around the tube guide and the tube, and
    wherein the strap includes a fastener to secure the strap at least partially around the tube and the tube guide.

3. The medical tube harness of claim 1, comprising a friction component disposed in the concave groove, the friction component in the form of a ridge transverse to the tube.

4. The medical tube harness of claim 1,
    wherein the leg garter includes at least one mounting element,
    wherein the at least one mounting element includes a slot to temporarily secure the tube guide to the garter, and
    wherein the slot is offset at an angle relative to an axis of the subject's leg so that when the subject transitions to a seated position, the tube guide disengages the slot and releases from the mounting element,
    whereby the tube guide disengaged from the slot and released from the mounting element prevents tugging on the tube within the tube guide, thereby preventing tug trauma to the subject.

5. The medical tube harness of claim 1,
    wherein the tube guide defines an opening,
    wherein a mounting element is joined with at least one of the belt, the shoulder strap and the garter,
    wherein the mounting element includes a pair of resilient fingers, selectively moveable toward and away from one another, the resilient fingers positioned in the opening so that the tube guide rotates relative to the mounting element.

6. The medical tube harness of claim 5 wherein the resilient fingers include enlarged ends that project beyond the opening to retain the tube guide in proximity to the mounting element.

7. The medical tube harness of claim 1,
    wherein the concave groove includes an entrance and an exit, with an inner contour extending between the entrance and the exit,
    wherein the inner contour is configured so that it redirects the tube from bearing along a first axis at the entrance to bearing along a second, different axis at the exit,
    whereby the tube guide redirects the tube from the first direction to the second direction without kinking the tube.

8. The medical tube harness of claim 1 wherein the concave groove includes an inner contour that redirects the tube from a first axis to a second, different axis, offset from the first axis at an angle,
    whereby the tube guide redirects the tube from the first direction to the second direction without kinking the tube.

9. A medical tube harness adapted for use on a subject, the harness comprising:
    a belt shaped and sized to fit around at least one of a subject's waist and torso;
    a plurality of shoulder straps extending upwardly from the belt, the shoulder straps shaped and sized to engage the subject's shoulders to thereby suspend the belt at least partially from the shoulders of the subject;
    a plurality of garters located below the belt, the garters shaped and sized to engage the subject's legs to thereby at least one of prevent and impair the belt from riding up the at least one of the subject's waist and torso;

at least one mounting element joined with at least one of the belt, the suspenders and the garters; and at least one tube guide joined with the mounting element, wherein the tube guide is moveable to a plurality of different mounting elements located on the at least one of the belt, the shoulder straps and the garters, to accommodate a plurality of different orientations of at least one tube associated with the subject;

wherein the tube guide defines a groove capturing and redirecting the tube from a first direction to a second, different direction, wherein the tube guide includes a tube lock that positions and immovably secures the tube to the tube guide, wherein the tube guide includes a rotational element that enables the tube guide, with a tube loaded thereon, to rotate about an axis of rotation, wherein the mounting element releasably receives the tube guide so that the tube guide is manually detachable, without the use of tools, from the mounting element joined with the at least one of the belt, the shoulder straps and the garters.

10. The medical tube harness of claim 9 comprising a friction component in the form of a friction enhancing coating disposed in the groove.

11. The medical tube harness of claim 9, wherein the groove has a u-shaped inner contour adapted to engage the tube when the tube is placed within the tube guide, the inner contour having a first radius that is larger than a radius of the tube, wherein the groove follows a contour curve that transitions the tube from the first direction to the second, different direction, the contour curve having a second radius larger than the first radius.

12. The medical tube harness of claim 9, wherein the groove is u-shaped and includes an entrance and an exit, wherein the entrance and the exit are offset at an angle relative to one another so that the tube is reoriented from the first direction to the second, different direction by the tube guide when the tube conforms to the u-shaped groove.

13. The medical tube harness of claim 12 wherein the angle is at least one of 45°, 60°, 75°, 90° and 105°.

14. The medical tube harness of claim 9, wherein the tube guide includes a tube guide flange extending from a lower portion of the groove generally opposite the inner contour, wherein the rotational element is mounted through a hole defined by the tube guide flange and extends generally perpendicular relative to the tube guide flange.

15. The medical tube harness of claim 14 wherein the rotational element includes a rotational element flange and at least one of a post and a fastener extending generally perpendicular to the flange.

16. The medical tube harness of claim 15, wherein the mounting element includes an opening in the form of a slot, wherein the at least one of a post and a fastener are removably positioned in the slot to secure the tube guide to the mounting element.

17. The medical tube harness of claim 9, wherein the mounting element defines a capture cavity and a slot, wherein the tube guide includes at least one of a post and a fastener that is joined with an enlarged head, wherein the enlarged head fits within the capture cavity when the at least one of a post and a fastener are located in the slot.

* * * * *